(12) United States Patent
McCormick

(10) Patent No.: US 7,975,586 B2
(45) Date of Patent: Jul. 12, 2011

(54) MICROTOME AND METHOD OF REVERSIBLY ALTERING A MICROTOME

(75) Inventor: James B. McCormick, Lincolnwood, IL (US)

(73) Assignee: Leica Biosystems Richmond, Inc., Richmond, IL (US)

( * ) Notice: Subject to any disclaimer, the term of this patent is extended or adjusted under 35 U.S.C. 154(b) by 1246 days.

(21) Appl. No.: 11/347,959

(22) Filed: Feb. 6, 2006

(65) Prior Publication Data

US 2007/0180964 A1 Aug. 9, 2007

(51) Int. Cl.
*B26D 1/00* (2006.01)
*B26D 7/06* (2006.01)
*B23Q 3/18* (2006.01)

(52) U.S. Cl. ............... 83/651; 83/76.9; 83/78; 83/915.5

(58) Field of Classification Search ................ 83/78, 13, 83/65, 76.9, 109, 409.1, 651, 730, 34, 36, 83/72, 76.8, 168, 915.5, 521, 522.12, 522.18, 83/707; 264/158; 269/11, 16, 55, 60, 56, 269/63, 71–73

See application file for complete search history.

(56) References Cited

U.S. PATENT DOCUMENTS

| | | | |
|---|---|---|---|
| 2,316,892 A | 4/1943 | Saul, Jr. | |
| 2,540,664 A | 2/1951 | Gluckman | |
| 2,761,813 A | 9/1956 | Goetz | |
| 2,800,102 A | 7/1957 | Welskopf et al. | |
| 2,837,055 A | 6/1958 | Whitehead | |
| 2,996,762 A | 8/1961 | McCormick | |
| 3,168,100 A | 2/1965 | Rich | |
| 3,195,502 A | 7/1965 | Levy | |
| 3,552,733 A * | 1/1971 | Pickett | 269/216 |
| 3,554,433 A | 1/1971 | Cardenaz | |
| 3,674,396 A | 7/1972 | McCormick | |
| 3,699,830 A * | 10/1972 | Pickett | 83/13 |
| 3,982,862 A | 9/1976 | Pickett et al. | |
| 4,421,246 A | 12/1983 | Schultz et al. | |
| 4,483,442 A | 11/1984 | Worth | |
| 4,501,363 A | 2/1985 | Isbey, Jr. | |

(Continued)

FOREIGN PATENT DOCUMENTS

EP 0 245 969 A2 11/1987

(Continued)

OTHER PUBLICATIONS

Int'l Search Report for PCT/US2005/042933, McCormick.

(Continued)

*Primary Examiner* — Ghassem Alie
(74) *Attorney, Agent, or Firm* — Thompson Coburn LLP

(57) ABSTRACT

A microtome includes a histological cassette support member that is adapted and configured to allow the microtome to be used in connection with relatively thin histological cassettes. A method of reversibly altering a microtome for use with different size histological specimen cassettes includes exchanging the cassette support member of the cassette holding assembly of the microtome with another cassette support member without altering other portions of the cassette holding assembly. A method is also disclosed that includes providing a microtome comprising a first histological tissue cassette clamp, providing a second histological tissue cassette clamp, securing the second histological tissue cassette clamp to the microtome via the first histological tissue cassette clamp, and securing a histological tissue cassette to the microtome via the second histological tissue cassette clamp when the second histological tissue cassette clamp is secured to the microtome via the first histological tissue cassette clamp.

8 Claims, 7 Drawing Sheets

U.S. PATENT DOCUMENTS

| | | |
|---|---|---|
| 4,549,670 A | 10/1985 | Trendler |
| 4,569,647 A | 2/1986 | McCormick |
| 4,576,796 A | 3/1986 | McCormick |
| 4,623,308 A | 11/1986 | Hellon |
| 4,684,013 A | 8/1987 | Jacobs |
| 4,801,553 A | 1/1989 | Owens et al. |
| 4,833,819 A | 5/1989 | Sherman |
| 4,834,943 A | 5/1989 | Yoshiyama |
| 5,061,452 A | 10/1991 | Yamamoto et al. |
| 5,080,869 A | 1/1992 | McCormick |
| 5,127,537 A | 7/1992 | Graham |
| 5,156,019 A | 10/1992 | McCormick |
| 5,269,671 A | 12/1993 | McCormick |
| 5,338,358 A | 8/1994 | Mizusawa et al. |
| 5,424,040 A | 6/1995 | Bjornsson |
| 5,427,742 A | 6/1995 | Holland |
| 5,543,114 A | 8/1996 | Dudek |
| 5,665,398 A | 9/1997 | McCormick |
| 5,673,905 A | 10/1997 | Kiene |
| 5,928,934 A | 7/1999 | McCormick |
| 6,231,037 B1 | 5/2001 | Metzner |
| 6,461,187 B2 | 10/2002 | Chen |
| 7,168,694 B2 * | 1/2007 | Bui et al. ............ 269/63 |
| 2004/0239024 A1 * | 12/2004 | Thiem ............ 269/55 |
| 2005/0112032 A1 | 5/2005 | McCormick |
| 2005/0112034 A1 | 5/2005 | McCormick |
| 2005/0115373 A1 * | 6/2005 | Kunkel ............ 83/168 |

FOREIGN PATENT DOCUMENTS

| | | |
|---|---|---|
| EP | 0312109 A2 | 4/1989 |
| EP | 0665424 A1 | 8/1995 |
| EP | 0807807 A1 | 11/1997 |
| EP | 1321757 A2 | 6/2003 |
| GB | A-2 189 599 | 10/1987 |
| WO | WO 95/09352 A1 | 4/1995 |

OTHER PUBLICATIONS

Leica Microsystems; "Leica RM2125 and RM2125RT"; Brochure; pp. 5; Leica Microsystems Nussloch GmbH, Nussloch.

Leica Microsystems; "Leica RM2125 Leica RM2125RT"; Instruction Manual; Mar. 2006; p. 1-40; Leica Microsystems Nussloch GmbH, Nussloch.

International Search Report and Written Opinion from corresponding International Application No. PCT/US2007/061562.

International Preliminary Report on Patentability (Chapter II) for PCT/US20071061562 issued Jun. 23, 2010.

Written Opinion of the International Preliminary Examining Authority for corresponding PCT/US20071061562 dated Mar. 31, 2010.

* cited by examiner

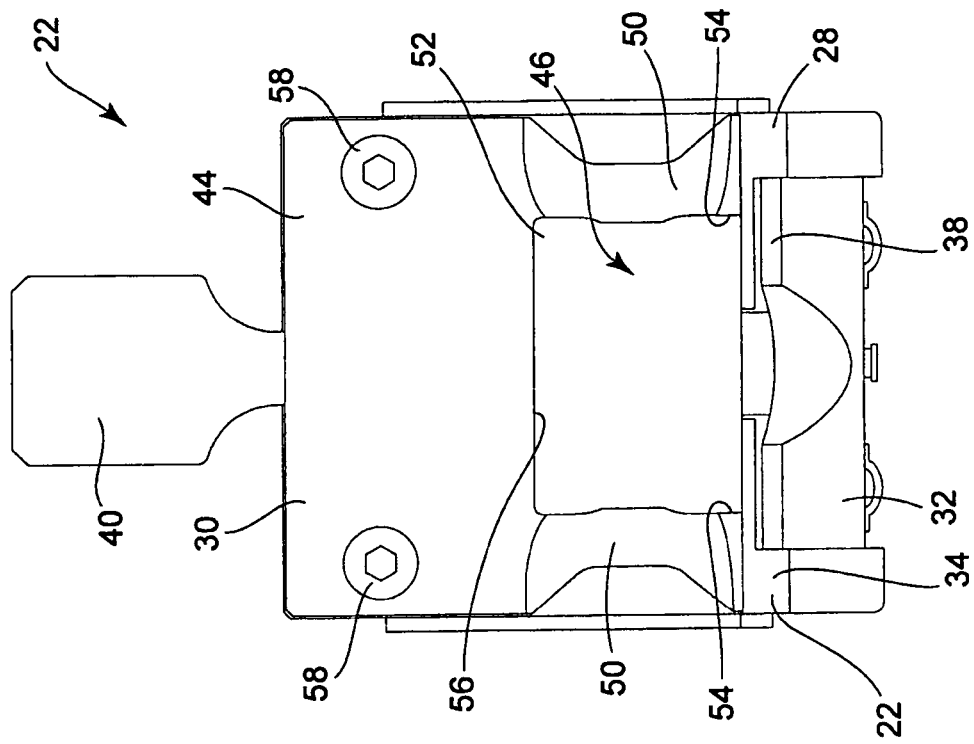
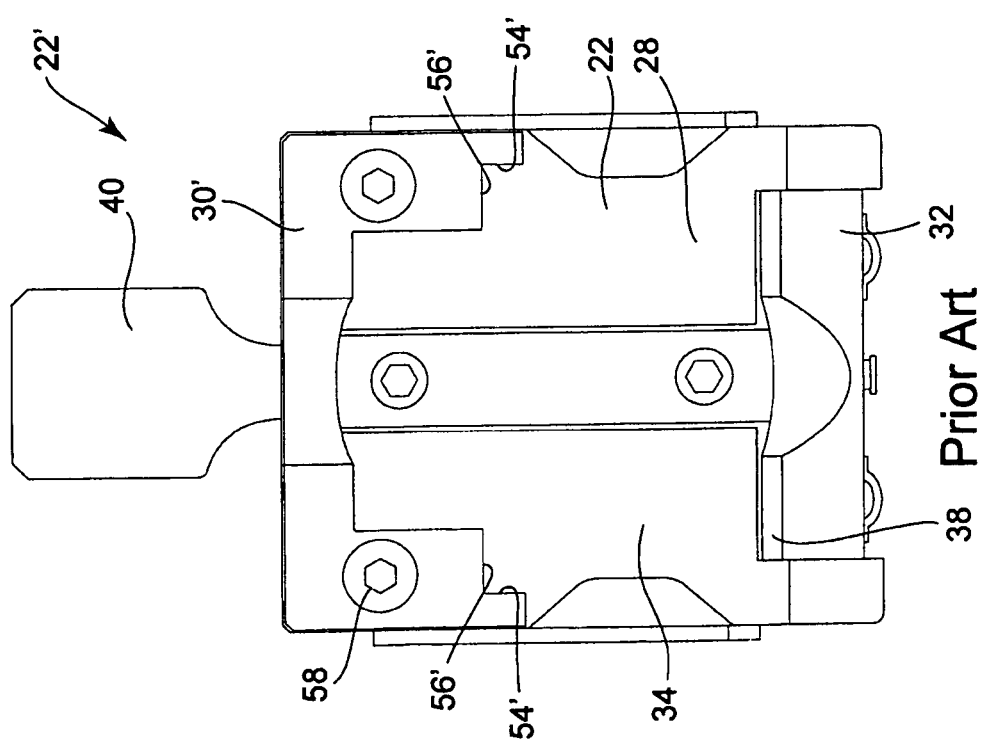
Prior Art
Figure 5
Figure 6

US 7,975,586 B2

MICROTOME AND METHOD OF REVERSIBLY ALTERING A MICROTOME

TECHNICAL FIELD OF THE INVENTION

The present invention pertains to the field of histological examination. More particularly, this invention pertains to a microtome having a histological cassette holder that is adapted and configured to releasably hold a relatively small histological cassette during the slicing of a tissue sample and to a method of reversibly altering a histological cassette holder to accommodate histological cassettes of different sizes.

BACKGROUND OF THE INVENTION

Microtomes utilize an extremely sharp blade to cut tissue specimens into thin slices for microscopic histological examination. Histological cassettes are often used to prepare tissue specimens for microscopic examination and to hold such tissue specimens during the slicing process.

During preparation of a tissue specimen, the tissue specimen is often placed in an interior compartment of a histological cassette and immersed in various fluids such as ethanol, xylene, formaldehyde, and water. After treatment of the tissue specimen is complete and prior to the slicing operation, the cassette and tissue sample are typically immersed in molten paraffin. The lid of the cassette is thereafter opened and tissue sample is removed from the cassette prior to the complete solidification of the paraffin. Following this step, the tissue sample is placed in a cavity formed in an embedding mold. The cassette is then placed above the tissue sample in the embedding mold and additional paraffin is used to secure the tissue sample to the exterior of the cassette adjacent the bottom surface of the cassette.

Microtomes are often fitted with cassette holding assemblies that are configured and adapted to securely hold a cassette and to pass very close to the blade of the microtome in a reciprocating manner. Additionally, the cassette holding assembly is typically able to move in very small and precise increments toward and away from the microtome blade in a direction perpendicular to the direction of reciprocation. Generally, a cassette is held by the cassette holding assembly in an orientation such that a tissue specimen, which is adhered to the cassette via solidified paraffin, engages the microtome blade with each reciprocating pass of the cassette holding assembly, thereby creating thin slices of the tissue specimens that are suitable for microscopic histological examination.

SUMMARY OF INVENTION

The present invention is directed to a microtome and a method of reversibly altering a microtome for use with different size histological specimen cassettes. In one aspect of the invention, a microtome is disclosed that comprises a microtome blade and a cassette clamp. The microtome blade has a blade edge. The cassette clamp comprises first, second, and third members. The first member has a generally planar surface and a pair of threaded openings. The second member comprises first and second surface portions and a pair of openings. The second member is removably engaged with and rigidly fixed to the first member in a manner such that the first surface portion of the second member is spaced at most a first distance from the planar surface of the first member and such that the pair of openings of the second member are aligned with the pair of openings of the first member. The second surface portion of the second member is spaced at least a second distance, which is greater than the first distance, from the planar surface of the first member. The third member comprises a clamping surface that opposes the second surface portion of the second member and that is movably connected to the first and second members in a manner such that the clamping surface is able to move toward and alternatively away from the second surface portion of the second member. The second and third members are adapted and configured in a manner such that a histological tissue cassette can be biased between the clamping surface of the third member and the second surface portion of the second member in a manner rigidly securing the histological tissue cassette to the cassette clamp. This is done with the histological tissue cassette engaging the first surface portion of the second member in a manner spacing the histological tissue cassette the first distance from the planar surface of the first member. The first, second, and third members are movable together relative to the microtome blade in a manner such that the second member can be positioned between the first member and the blade edge of the microtome blade.

In another aspect of the invention, a microtome is disclosed that comprises a microtome blade and a cassette clamp. The microtome blade has a blade edge. The cassette clamp has first, second, and third members. The first member of the cassette clamp has a generally planar surface and a pair of threaded openings. The second member has a pair of openings, first and second opposing surface portions, and a third surface portion. The second member is removably engaged with and rigidly fixed to the first member in a manner such that the pair of openings of the second member are aligned with the pair of openings of the first member. The third member comprises a clamping surface that opposes the third surface portion of the second member and that is movably connected to the first and second members in a manner such that the clamping surface is able to move toward and alternatively away from the third surface portion of the second member. The opposing surface portions of the second member are closer to the clamping surface of the third member than to third surface portion of the second member. The second and third members are adapted and configured in a manner such that a histological tissue cassette can be biased between the clamping surface of the third member and the third surface portion of the second member with the histological tissue cassette positioned between the opposing surfaces of the second member. The first, second, and third members are movable together relative to the microtome blade in a manner such that the second member can be positioned between the first member and the blade edge of the microtome blade.

In yet another aspect of the invention, a method is disclosed that comprises a step of providing a microtome. The microtome comprises a microtome blade and a cassette clamp. The microtome blade has a blade edge. The cassette clamp has a pair of threaded fasteners and first, second, and third members. The first member has a generally planar surface and a pair of threaded openings. The second member has a pair of openings and a first surface portion. The second member is removably engaged with and rigidly fixed to the first member by the fasteners which pass through the pair of openings of the second member and are threadably engaged with the openings of the first member. The third member comprises a clamping surface that opposes the first surface portion of the second member and that is movably connected to the first member in a manner such that the clamping surface is able to move toward and alternatively away from the protrusion of the second member. The second and third members define a first distance that is a closest distance that the clamping surface of the third member is able to move toward the first surface portion of the second member. The second and third members are adapted and configured in a manner such that a histological tissue cassette can be biased between the clamping surface of the third member and the first surface portion of the second member. The first, second, and third members are movable together relative to the microtome blade in a manner such that the second member can be positioned between the first member and the blade edge of the microtome blade.

This method further comprises a step of removing the second member of the cassette clamp from the first and third members and thereafter attaching a fourth member to the cassette clamp in place of the second member. The removing of the second member from the first and third members comprises threadably disengaging the fasteners from the openings of the first member. The fourth member has a pair of openings and a first surface portion. The attaching of the fourth member to the cassette clamp occurs in a manner such that the fourth member is removably engaged with and rigidly fixed to the first member by the fasteners, which pass through the pair of openings of the fourth member and are threadably engaged with the openings of the first member. The attaching of the fourth member to the cassette clamp also occurs in a manner such that the fourth and third members are adapted and configured to bias a histological tissue cassette between the clamping surface of the third member and the first surface portion of the fourth member and such that the fourth and third members define a second distance that is a closest distance that the clamping surface of the third member is able to move toward the first surface portion of the fourth member. The second distance is less than the first distance.

In still another aspect of the invention, a first histological tissue cassette clamp is disclosed that comprises a first portion, a second portion, and a fitting. The first portion is movable relative to the second portion in a manner such that the first histological tissue clamp is adapted and configured to securely hold a first histological tissue cassette. The fitting is sized and shaped in a manner such that the fitting can be held by a second histological tissue cassette clamp that is adapted and configured to securely hold a second histological tissue cassette that differs in size from the first histological tissue cassette.

In yet another aspect of the invention, a method is disclosed that comprises the steps of providing a microtome that comprises a first histological tissue cassette clamp and providing a second histological tissue cassette clamp. The method further comprises a step of securing the second histological tissue cassette clamp to the microtome via the first histological tissue cassette clamp. Additionally, the method comprises a step of securing the histological tissue cassette to the microtome via the second histological tissue cassette clamp when the second histological tissue cassette clamp is secured to the microtome via the first histological tissue cassette clamp.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which:

FIG. 5 is a front elevation view of the prior art cassette holding assembly of FIG. 2 with the prior art cassette support member of FIG. 4 attached thereto;

FIG. 6 is a front elevation view of the prior art cassette holding assembly of FIG. 2 with the cassette support member of FIG. 3 attached thereto;

Figure 1:
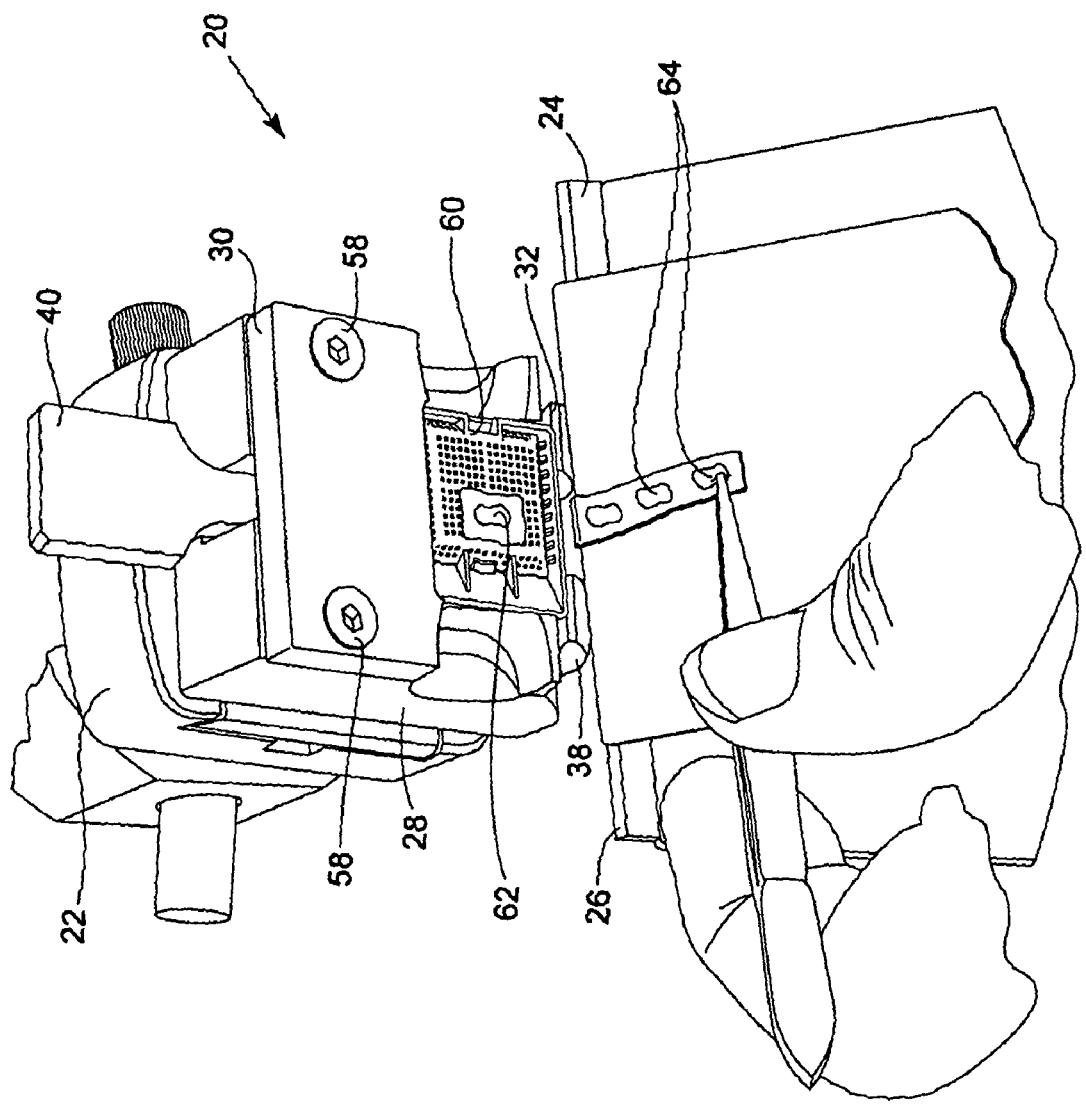
FIG. 1 is a perspective view of a microtome in accordance with the invention being used to create slices of a tissue specimen for histological examination in connection with a microscope.

Reference characters in the written specification indicate corresponding items shown throughout the drawing figures.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so that the present invention will not be obscured.

An embodiment of a microtome in accordance with the invention is depicted in FIG. 1. The microtome 20 comprises a cassette holding assembly 22 and a microtome blade 24. The cassette holding assembly 22 is connected to the microtome blade 24 in a manner such that the cassette holding assembly is able to move vertically behind the microtome blade in a reciprocating manner and such that the horizontal distance between the cassette holding assembly and the cutting edge 26 of the microtome blade can be incrementally adjusted with precision.

The cassette holding assembly 22 comprises a base member 28, a cassette support member 30, and a clamping member 32. The microtome 20 is preferably formed by modifying a prior art microtome, such as a Leica® model number RM 2125 RT. Leica® is a federally registered trademark of Leica Microsystems Nussloch GmbH, having a place of business at Heidelberger Strasse 17-19, D-69226 Nussloch, Germany. The base member 28 and the clamping member 32 of the microtome 20 are preferably unaltered from their original configuration. The cassette support member 30 is entirely new.

Figure 2:
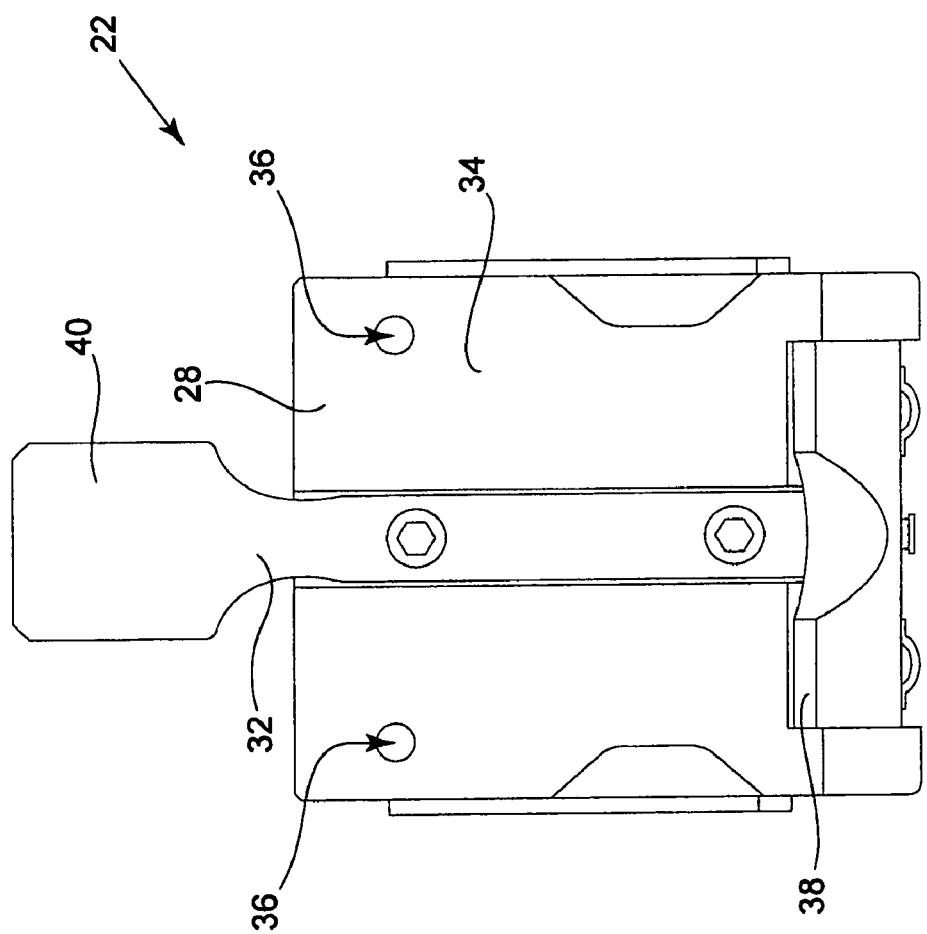
FIG. 2 is a front elevation view of a prior art cassette holding assembly with its cassette support member removed.

The base member 28 of the cassette holding assembly 22 comprises a vertically oriented planar surface 34 and a pair of threaded openings 36 (as shown in FIG. 2) that extend into base member perpendicular to the planar surface. The clamping member 32 is movably connected to the base member 28 and comprises a clamping portion 38 that is moveable vertically relative to the base member. A clamping handle 40 is preferably utilized to adjust the vertical position of the clamping portion 38 of the clamping member 32 relative to the base member 28.

Figure 3:
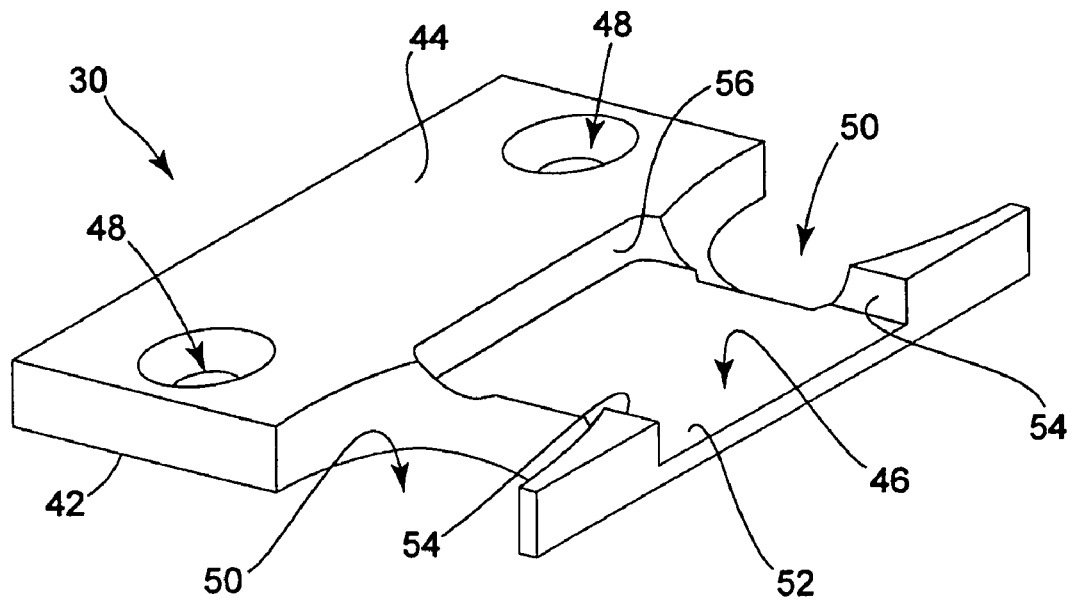
FIG. 3 is a perspective view of a cassette support member in accordance with the invention.
Figure 4:
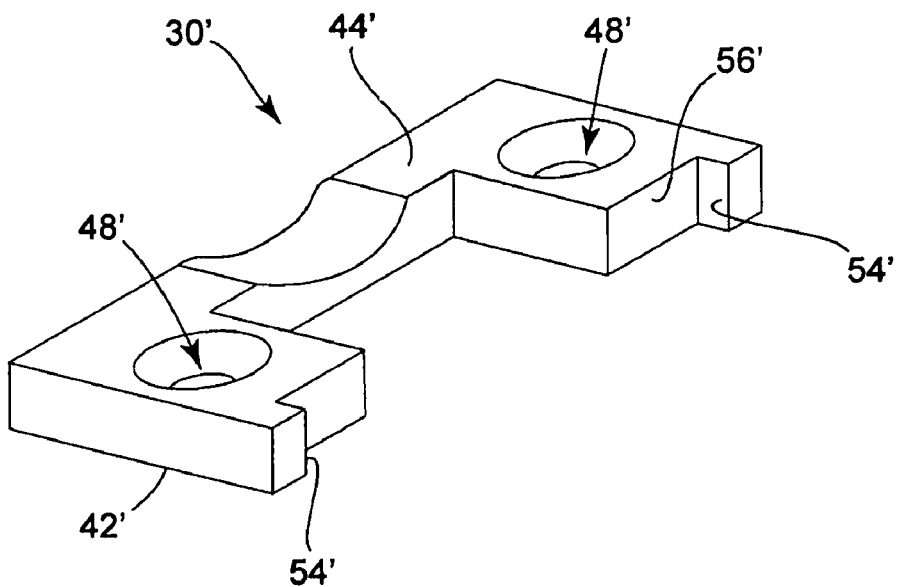
FIG. 4 is a perspective view of a prior art cassette support member.

The cassette support member 30 is shown by itself in FIG. 3 and a prior art cassette support member 30' is shown by itself in FIG. 4. The cassette support member 30 comprises a planar rear surface 42, a planar front surface 44, a recess 46, a pair of countersunk holes 48, and a pair of access openings 50. The recess 46 extends towards the rear surface 42 from the front surface 44 and extends out of the bottom of the cassette support member 30. The recess 46 preferably forms a planar recessed surface 52 that is parallel to the rear surface 42, two opposing vertical side surfaces 54, and a downward facing surface 56. The opposing side surfaces 54 preferably protrude perpendicularly from the recessed surface 52 and the downward facing surface preferably protrudes in a horizontal manner from the recessed surface above the side surfaces 52.

It should be appreciated that many of the features of the cassette support member 30 are not found on the prior art cassette support member 30'. For example, the prior art cassette support member 30' lacks a recessed surface. Although the prior art cassette support member 30' does comprise opposing vertically oriented side surfaces 54' and a downward facing surface 56' thereabove, each of these surfaces extends completely through the prior art cassette support member from the front surface 44' to the rear surface 42' of the prior art cassette support member. However, the countersunk holes 48 of the new cassette support member 30 are preferably identical to the countersunk holes 48' of the prior art cassette support member 30'.

As shown in FIGS. 5 and 6, the cassette support member 30 is adapted and configured to be secured to the base member 28 of the microtome 20 in place of the prior art cassette support member 30'. To do this, the fasteners 58, which extend through the counter sunk holes 48' of the prior art cassette support member 30' and into the threaded openings 36 of the base member 28, are unscrewed and removed. This unsecures the prior art cassette support member from the base member 28. The new cassette support member 30 is then positioned against the base member 28 with the rear surface 42 of the cassette support member engaging the planar surface 34 of the base member and with the countersunk holes 48 of the cassette support member aligned with the threaded openings 36 of the base member. Preferably, the same fasteners 58 that were used to secure the prior art cassette support member 30' to the base member 28 are then inserted through the counter sunk holes 48 of the new cassette member 30 and are screwed into the threaded holes 36 of the base member. These steps can be reversed, thereby allowing the microtome 20 to be switched back and forth between the new cassette holding assembly 22 and the prior art cassette holding assembly 22'.

Figure 8:
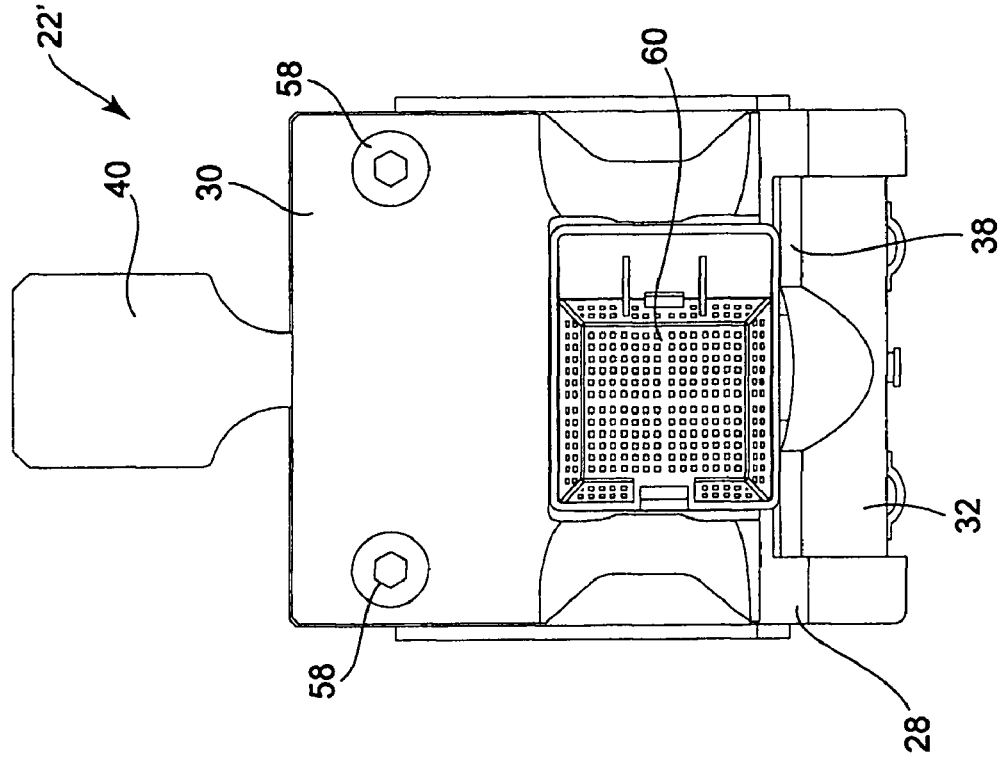
FIG. 8 is a front elevation view of the cassette holding assembly shown in FIG. 6 holding a histological cassette.
Figure 7:
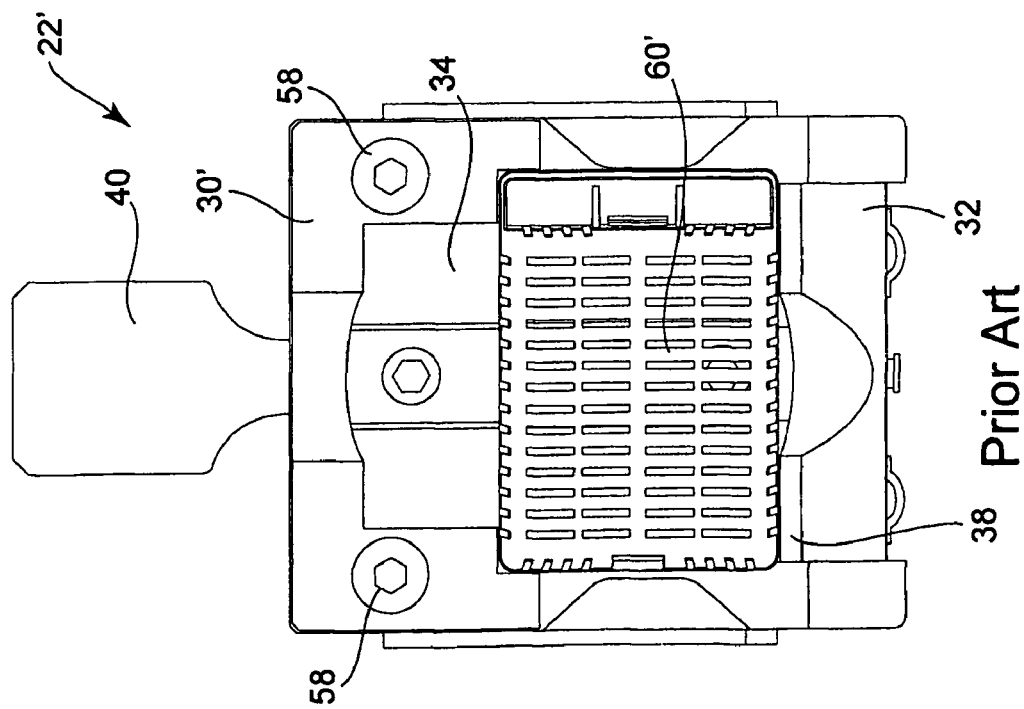
FIG. 7 is a front elevation view of the prior art cassette holding assembly shown in FIG. 5 holding a histological cassette.

As shown in FIGS. 7 and 8, the new cassette support member 30 allows the cassette holding assembly 22 to hold a histological cassette 60 that is much smaller than can be held by the prior art cassette holding assembly 22'.

When using the prior art cassette holding assembly 22', a histological cassette 60' is placed against the planar surface 34 of the base member 28 where it is positioned between the opposing side surfaces 54' of the prior art cassette support member 30', and between the downward facing surface 56' of the prior art cassette support member and the clamping portion 38 of the clamping member 32. The clamping member 32 is then utilized to bias the histological cassette 60' between the clamping portion 38 of the clamping member and the downward facing surface 56' of the prior art cassette support member 30'. As this is performed, the opposing side surfaces 54' of the prior art cassette support member 30' act to limit side-to-side translation of the histological cassette 60' relative to the cassette holding assembly 22'.

In contrast, when using the cassette holding assembly 22 of the invention, a histological cassette 60 is placed against the recessed surface 52 of the cassette support member 30 in a manner such that the histological cassette is spaced a distance from the planar surface 34 of the base member 28. This allows the histological cassette 60 to be made thinner without changing the relative horizontal position of the exposed surface of the histological cassette relative to the cutting edge 26 of the microtome blade 24. In other words, the distance between the recessed surface 52 of the cassette support member 30 and the planar surface 34 of the base member 28 can be set to compensate for the difference between the thickness of a histological cassette of the type that the cassette holding assembly was originally configured to hold and the thickness of a thinner histological cassette. Additionally, the downward facing surface 56 of the cassette support member 30 is positioned closer to the clamping portion 38 of the clamping member 32, as compared to the downward facing surface 56' of the prior art cassette support member 30'. This allows narrower histological cassettes 60 to be held without altering the clamping member 32 of the cassette holding assembly 22. Still further, unlike the prior art cassette support member 30', the opposing side surfaces 54 of the cassette support member 30 have portions that are positioned closer to the clamping portion 38 of the clamping member 32 than to the downward facing surface 56 of the cassette support member. This improves the ability of opposing side surfaces 54 of the cassette support member 30 to limit side to side translation of the histological cassette 60 relative to the cassette holding assembly 22, and prevents the histological cassette 60 from rotating when it is initially placed in the recess 46 of the cassette support member. The access openings 50 of the cassette support member 30 allow the relatively small histological cassette 60 to be easily gripped when it is being attached to and removed from the cassette holding assembly 22.

FIG. 1 depicts a microtome 20 in accordance with the invention being used to cut a tissue specimen 62 into thin slices 64 for microscopic histological examination. Each time the cassette holding assembly 22 is brought down behind the microtome blade 24, a slice 64 of the tissue specimen can be cut from the tissue specimen. In view of the present invention, it should be appreciated that no alteration to the microtome 20 other than to the cassette support member 30 is necessary to allow the microtome to be used with relatively small histological cassettes 60.

Figure 9:
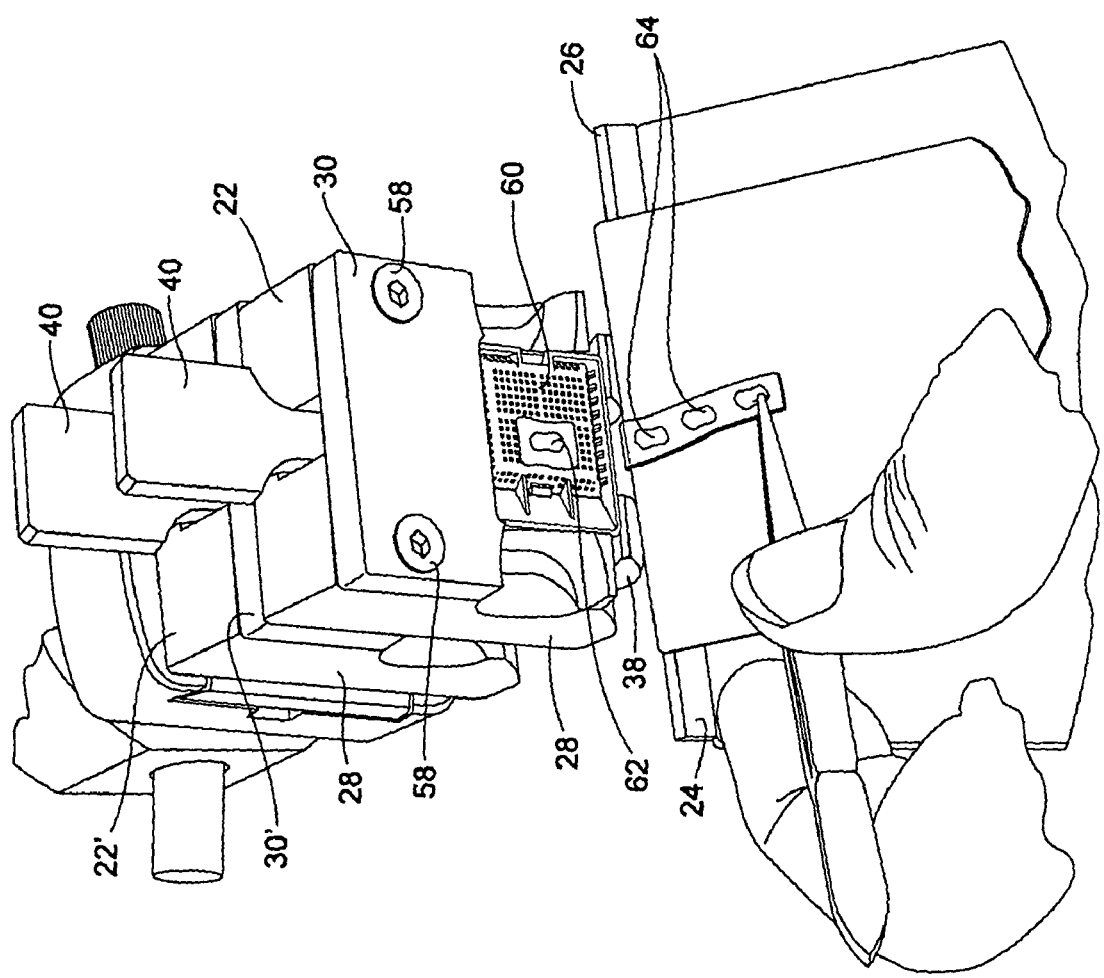
FIG. 9 is a perspective view of microtome comprising a first clamp and a second clamp, the first clamp holding a histological cassette and the second clamp holding the first clamp to the microtome.
Figure 10:
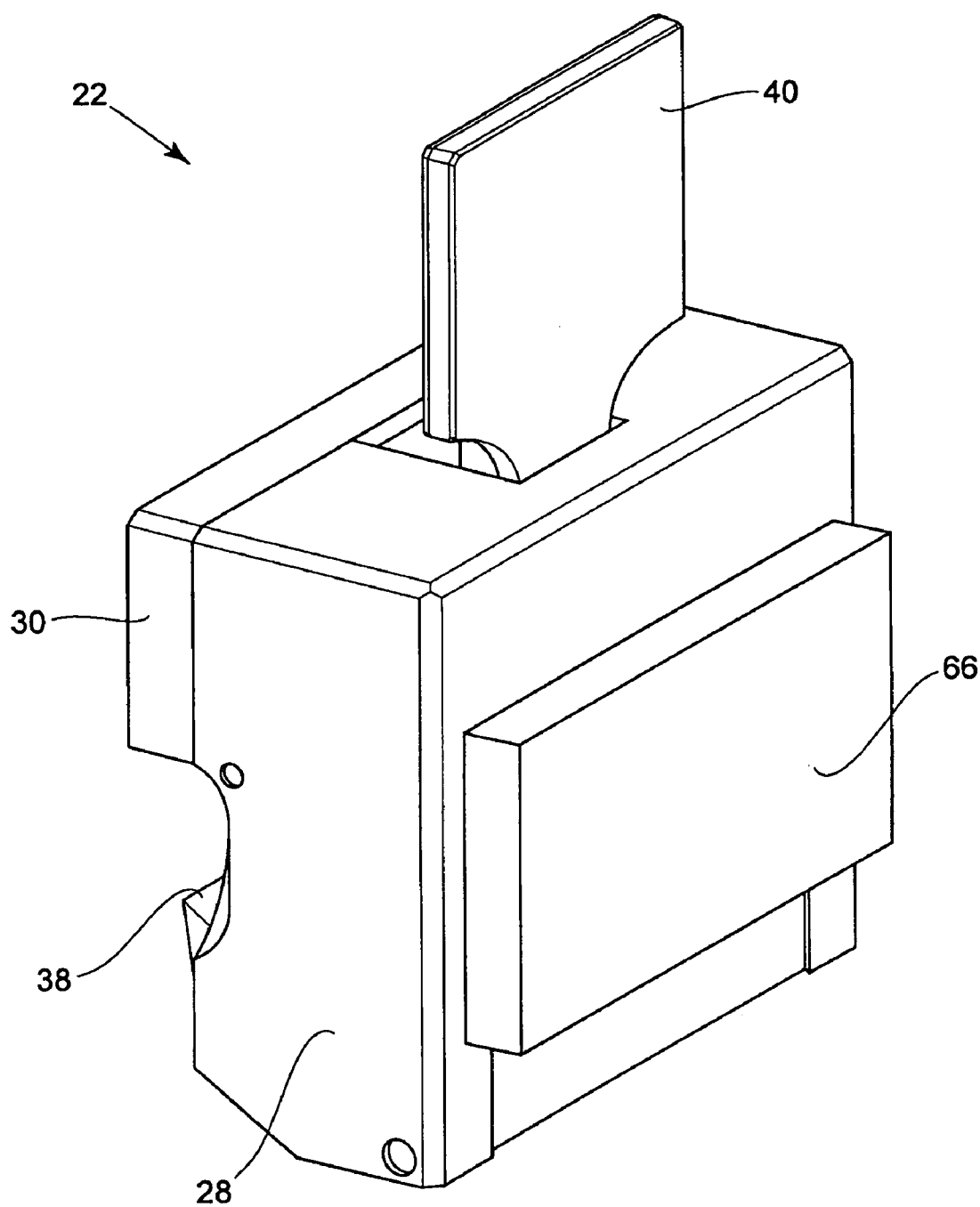
FIG. 10 is a rear perspective view of the first clamp shown in FIG. 9.

A second and preferred embodiment of the invention is shown in FIGS. 9 and 10. The second embodiment of the invention pertains to the concept of providing a histological tissue cassette holding assembly 22 that is configured and adapted to hold the smaller histological tissue cassettes. The histological tissue cassette holding assembly 22 includes a fitting 66 that is shaped similar to a larger histological tissue cassette such that the histological tissue cassette holding assembly 22 can be held by a prior art histological tissue cassette holding assembly 22' of a microtome. In other words, the second embodiment of the invention utilizes a second histological tissue cassette clamp that can be held by the histological tissue cassette clamp of a prior art microtome for quickly adapting the microtome for use in connection with a histological tissue cassette that differs in size from the histological tissue cassettes held by the prior art histological tissue cassette clamp. The histological tissue cassette holding assembly 22 could be any type of histological tissue cassette clamp, including the first embodiment previously discussed above. As shown in FIG. 10, the rear of the histological tissue cassette holding assembly 22 comprises a fitting 66 that allows the histological tissue cassette holding assembly to be held by another histological tissue cassette clamp. The fitting 66 is preferably rectangular in shape and is preferably dimensioned to be similar, if not identical, in size to a common 28 millimeter by 40 millimeter histological tissue specimen cassette known in the prior art. The fitting 66 is preferably, but not necessarily, formed out of metal and can be formed as an integral portion of some other part of the histological tissue cassette holding assembly 22, or can be a separate part attached to the remainder of the histological tissue cassette holding assembly 22 via fasteners or other means. By being shaped similar to a standard prior art 28 millimeter by 40 millimeter histological tissue cassette, the fitting 66 allows the histological tissue cassette holding assembly 22 to be held by any prior art histological tissue cassette clamp that is configured to hold 28 millimeter by 40 millimeter histological tissue cassettes.

While the present invention has been described in reference to a specific embodiment, in light of the foregoing, it should be understood that all matter contained in the above description or shown in the accompanying drawings is intended to be interpreted as illustrative and not in a limiting sense and that various modifications and variations of the invention may be constructed without departing from the scope of the invention defined by the following claims. Thus, other possible variations and modifications should be appreciated.

Furthermore, it should be understood that when introducing elements of the present invention in the claims or in the above description of the preferred embodiment of the invention, the terms "comprising," "including," and "having" are intended to be open-ended and mean that there may be additional elements other than the listed elements. Similarly, the term "portion" should be construed as meaning some or all of the item or element that it qualifies.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

The invention claimed is:

1. A microtome comprising:
    a microtome blade, the microtome blade having a blade edge; and
    a cassette clamp, the cassette clamp having first, second, and third members, the first member having a generally planar surface and a pair of threaded openings, the second member having first and second surface portions and a pair of openings, the second member being removably engaged with and rigidly fixed to the first member in a manner such that the first surface portion of the second member is spaced at most a first distance from the planar surface of the first member and the pair of openings of the second member are aligned with the pair of openings of the first member, the second surface portion of the second member being spaced at least a second distance from the planar surface of the first member, the second distance being greater than the first distance, the third member comprising a clamping surface that opposes the second surface portion of the second member and that is movably connected to the first and second members in a manner such that the clamping surface is able to move toward and alternatively away from the second surface portion of the second member, the second and third members being adapted and configured in a manner such that a histological tissue cassette can be held between the clamping surface of the third member and the second surface portion of the second member having opposing vertically oriented side surfaces and a downward facing surface with the histological tissue cassette engaging the first surface portion of the second member in a manner rigidly securing the histological tissue cassette to the cassette clamp while also spacing the histological tissue cassette the first distance from the planar surface of the first member, the first, second, and third members being movable together relative to the microtome blade in a manner such that the second member can be positioned between the first member and the blade edge of the microtome blade, wherein the second member further comprises opposing surface portions, and wherein the second and third members are adapted and configured in a manner such that a histological tissue cassette can be held between the clamping surface of the third member and the second surface portion of the second member with the histological tissue cassette being positioned between the opposing surface portions of the second member and with the histological tissue cassette engaging the first surface portion of the second member in a manner rigidly securing the histological tissue cassette to the cassette clamp while also spacing the histological tissue cassette the first distance from the planar surface of the first member.

2. The microtome in accordance with claim 1, wherein the first surface portion of the second member is planar and is parallel to the planar surface of the first member.

3. The microtome in accordance with claim 2, wherein the second surface portion of the second member is oriented perpendicular to the first surface portion of the second member.

4. The microtome in accordance with claim 3, wherein the second surface portion of the second member is planar and intersects the first surface portion of the second member in a manner defining a linear coterminous edge shared by the first and second surface portions of the second member.

5. The microtome in accordance with claim 1, wherein the opposing surface portions are closer to the clamping surface of the third member than to the second surface portion of the second member.

6. The microtome in accordance with claim 1, wherein the opposing surface portions are planar and are parallel to each other.

7. The microtome in accordance with claim 6, wherein the first surface portion of the second member is planar and is parallel to the planar surface of the first member, and wherein the opposing surface portions of the second member are perpendicular to the first surface portion of the second member.

8. The microtome in accordance with claim 7, wherein the second surface portion of the second member is planar and is oriented perpendicular to the first surface portion of the second member and to each of opposing surface portions of the second member.

* * * * *